United States Patent
Holman et al.

(10) Patent No.: US 8,690,824 B2
(45) Date of Patent: Apr. 8, 2014

(54) MEDICAL DEVICES AND RELATED METHODS

(75) Inventors: Thomas J. Holman, Princeton, MN (US); James Lee Shippy, III, Wilmington, NC (US); Afsar Ali, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/441,664

(22) Filed: Apr. 6, 2012

(65) Prior Publication Data

US 2012/0197380 A1    Aug. 2, 2012

Related U.S. Application Data

(62) Division of application No. 11/599,052, filed on Nov. 14, 2006, now Pat. No. 8,153,181.

(51) Int. Cl.
*A61M 31/00* (2006.01)
*A61M 37/00* (2006.01)

(52) U.S. Cl.
USPC ............ 604/103.02; 604/103.08; 604/103.14; 606/194

(58) Field of Classification Search
USPC .......................... 604/103.02, 103.06–103.08, 604/103.11–103.14; 606/192, 194; 623/1.11
See application file for complete search history.

(56) References Cited

U.S. PATENT DOCUMENTS

| | | | |
|---|---|---|---|
| 4,976,690 A * | 12/1990 | Solar et al. ............... | 604/103.06 |
| 5,209,799 A | 5/1993 | Vigil | |
| 5,509,899 A | 4/1996 | Fan | |
| 5,693,014 A | 12/1997 | Abele | |
| 5,746,745 A * | 5/1998 | Abele et al. ................. | 623/1.11 |
| 5,976,155 A | 11/1999 | Foreman | |
| 6,010,480 A | 1/2000 | Abele | |
| 6,610,035 B2 | 8/2003 | Yang | |
| 6,673,053 B2 | 1/2004 | Wang | |
| 6,786,889 B1 | 9/2004 | Musbach | |
| 6,960,187 B2 | 11/2005 | Kastenhofer | |
| 7,413,558 B2 * | 8/2008 | Kelley et al. ............. | 604/103.08 |
| 2003/0083579 A1 | 5/2003 | Aita | |
| 2003/0163157 A1 | 8/2003 | McMorrow et al. | |
| 2004/0133223 A1 | 7/2004 | Weber | |
| 2006/0020243 A1 | 1/2006 | Speck | |
| 2006/0129179 A1 | 6/2006 | Weber | |
| 2006/0182873 A1 | 8/2006 | Klisch | |
| 2007/0060863 A1 | 3/2007 | Goeken | |
| 2007/0129748 A1 * | 6/2007 | Eidenschink et al. ........ | 606/192 |
| 2007/0247033 A1 | 10/2007 | Eidenschink | |
| 2008/0065188 A1 | 3/2008 | Pallazza | |
| 2008/0114294 A1 | 5/2008 | Holman | |

FOREIGN PATENT DOCUMENTS

DE     10244847     4/2004

\* cited by examiner

*Primary Examiner* — Theodore Stigell
(74) *Attorney, Agent, or Firm* — Vidas, Arrett & Steinkraus

(57) ABSTRACT

This disclosure relates to medical devices and related methods. In some embodiments, the methods include applying a material to the balloon and then removing the material from one or more regions of the balloon.

14 Claims, 8 Drawing Sheets

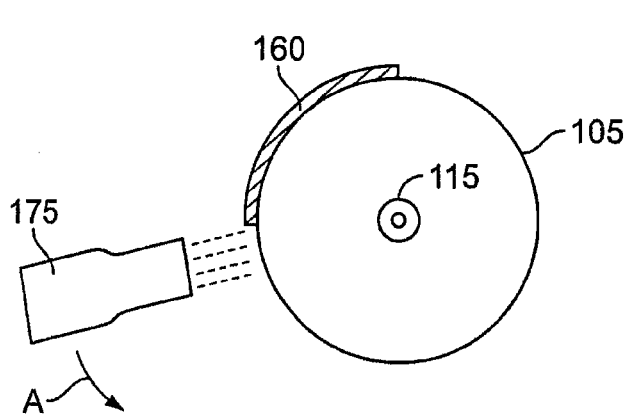
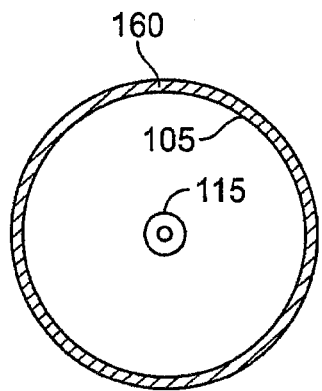
FIG. 6A          FIG. 6B
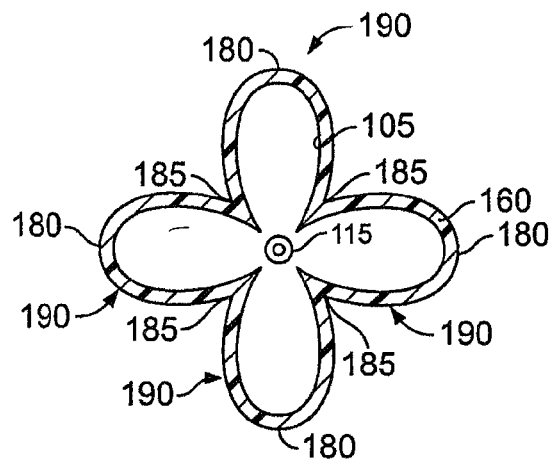
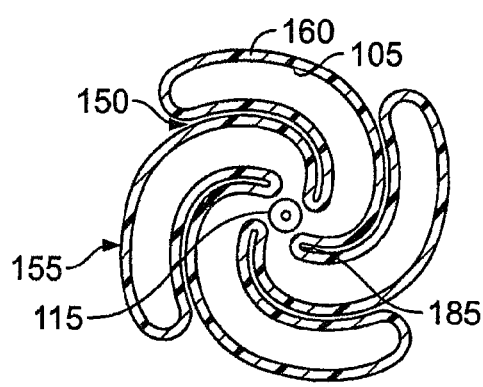
FIG. 6C          FIG. 6D
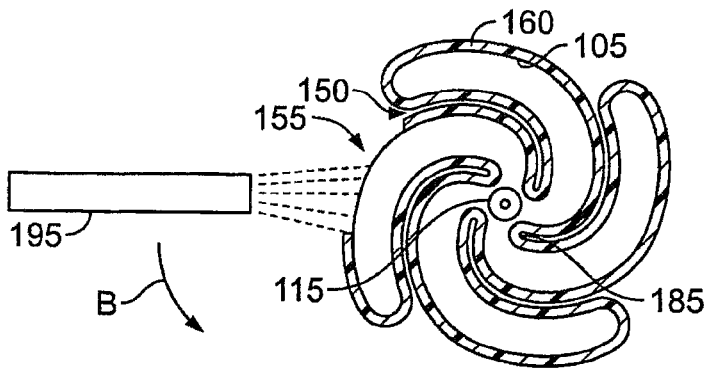
FIG. 6E

MEDICAL DEVICES AND RELATED METHODS

CROSS-REFERENCE TO RELATED APPLICATIONS

This application is a divisional application of U.S. patent application Ser. No. 11/599,052, filed on Nov. 14, 2006, the entire content of which is incorporated herein by reference.

TECHNICAL FIELD

This disclosure relates to medical devices and related methods.

BACKGROUND

Balloon catheters can be used for a variety of medical procedures such as, for example, to widen an occluded body vessel, as in angioplasty, to position a medical device, such as a stent or a graft, or to selectively block a passageway. A balloon catheter may include an inflatable and deflatable balloon positioned on a catheter body. Initially, the balloon is folded around the catheter body to reduce the radial profile of the balloon catheter for easy insertion into the body.

During use, for example, in angioplasty, the folded balloon can be positioned at a location in a vessel occluded by a stenosis by threading the balloon catheter through a guide catheter and over a guide wire emplaced in the body. The balloon is then inflated, e.g., by introducing a fluid into the interior of the balloon. Inflating the balloon can radially expand the stenosis to permit increased blood flow through the vessel. After expanding the stenosis, the balloon is deflated and withdrawn from the body.

SUMMARY

In one aspect of the invention, a method includes applying a material to an at least partially inflated medical balloon, folding the medical balloon, and, after folding the medical balloon, removing at least some of the material exposed about an outer surface of the folded medical balloon.

In another aspect of the invention, a method includes applying a material to a medical balloon and removing the material overlying one or more fold regions of the medical balloon. The material applied to the medical balloon has a coefficient of friction different than a coefficient of friction of the medical balloon.

In a further aspect of the invention, a balloon catheter includes a balloon folded about a catheter shaft. The folded balloon includes outer fold regions that are substantially exposed about an outer surface of the folded balloon and inner fold regions that are substantially unexposed about the outer surface of the folded balloon. The inner fold regions are coated with a material and the outer fold regions are substantially free of the material.

Embodiments can include one or more of the following features.

In some embodiments, after removing the material, one or more inner fold regions of the balloon include the material thereon, and one or more outer fold regions of the balloon include substantially none of the material thereon.

In some embodiments, upon inflating the medical balloon, one or more regions of an outer surface of the inflated medical balloon include the material thereon and one or more regions of the outer surface of the inflated medical balloon include substantially none of the material thereon.

In some embodiments, the material has a coefficient of friction different than (e.g., greater than or less than) a coefficient of friction of the medical balloon.

In certain embodiments, the material is a lubricant.

In some embodiments, applying the material to the medical balloon includes using one or more of the following material application techniques: spraying, painting, dip coating, and pad printing.

In certain embodiments, removing the material includes applying laser energy (e.g., laser energy has a wavelength of about 157 nm to about 355 nm) to the material.

In some embodiments, the method includes passing the laser energy through a masking device.

In certain embodiments, removing the material includes removing the material from substantially the entire surface of a portion of the folded balloon.

In some embodiments, the material is removed from a body portion of the folded balloon.

In certain embodiments, the material is removed from substantially an entire exposed outer surface of the folded balloon.

In some embodiments, the method includes deflating the medical balloon after applying the material to the medical balloon.

In certain embodiments, the method includes disposing an implantable medical endoprosthesis about the folded medical balloon.

In some embodiments, the implantable medical endoprosthesis is disposed about the folded medical balloon after the material is removed from the medical balloon.

In certain embodiments, the implantable medical endoprosthesis is a stent.

In some embodiments, the method includes folding the medical balloon.

In certain embodiments, after folding the medical balloon, one or more outer fold regions are exposed about an outer surface of the folded medical balloon and one or more inner fold regions are substantially unexposed about the outer surface of the folded medical balloon.

In some embodiments, the one or more fold regions include one or more inner fold regions of the medical balloon.

In certain embodiments, the one or more fold regions include one or more outer fold regions of the medical balloon.

In some embodiments, after removing the material, one or more inner fold regions of the balloon include the material thereon, and one or more outer fold regions of the balloon include substantially none of the material thereon.

In certain embodiments, after removing the material, one or more outer fold regions of the balloon include the material thereon, and one or more inner fold regions of the balloon include substantially none of the material thereon.

In some embodiments, upon inflating the medical balloon, one or more regions of an outer surface of the inflated medical balloon include the material thereon and one or more regions of the outer surface of the inflated medical balloon include substantially none of the material thereon.

In certain embodiments, the medical balloon is at least partially inflated when the material is applied to the medical balloon.

In some embodiments, the method includes deflating the inflatable medical balloon after removing the material from the medical balloon.

In certain embodiments, the material is removed from substantially only the one or more fold regions of the medical balloon.

In some embodiments, the method further includes treating the medical balloon to form the one or more fold regions.

In certain embodiments, the medical balloon is treated before removing the material from the medical balloon.

In some embodiments, treating the medical balloon includes applying laser energy to the inflatable medical balloon.

In certain embodiments, upon inflating the balloon, both the inner and outer fold regions are exposed about an outer surface of the inflated balloon.

Embodiments can include one or more of the following advantages.

In some embodiments, the balloon is configured such that, when the balloon is deflated and folded, substantially only regions having a relatively high coefficient of friction is/are exposed about the outer surface of the balloon, and such that, when the balloon is inflated, both the regions having a relatively high coefficient of friction and regions having a relatively low coefficient of friction are exposed about the outer surface of the balloon. As a result of this configuration, the balloon can help to restrain (e.g., axially and/or circumferentially restrain) the implantable medical endoprosthesis thereon when the balloon is delivered through a body vessel in the deflated state, and can help to reduce the amount of friction experienced by the balloon as the balloon is removed from the deployed medical endoprosthesis after being inflated to deploy the implantable medical endoprosthesis within the body vessel.

In certain embodiments, the balloon is configured such that, when the balloon is deflated and folded, substantially only the regions having a relatively low coefficient of friction is/are exposed about the outer surface of the balloon, and such that, when the balloon is inflated, both the regions having a relatively low coefficient of friction and regions having a relatively high coefficient of friction are exposed about the outer surface of the balloon. This configuration can help to reduce the friction encountered by the folded balloon as it is delivered through the body vessel, and can help to increase frictional resistance between the balloon and the body vessel wall, and thus stabilize the balloon, when the balloon is inflated within the body vessel, e.g., during an angioplasty procedure.

In some embodiments, laser energy is applied to desired regions of the material (e.g., the lubricant) to remove the material from the balloon surface. Using laser energy to remove the material can, for example, allow the material to be removed with sufficient accuracy to ensure that material is removed from substantially only desired regions of the balloon surface. In certain embodiments, the material (e.g., the lubricant) is cured to help prevent the material remaining on the balloon surface from migrating into those regions of the balloon surface from which the material was removed.

Other aspects, features, and advantages will be apparent from the description, drawings, and claims.

DESCRIPTION OF DRAWINGS

FIGS. 6A-6G illustrate an embodiment of a method of manufacturing a balloon catheter.

Like reference symbols in the various drawings indicate like elements.

DETAILED DESCRIPTION

Described are methods that include applying a material (e.g., a lubricant) to a medical balloon, and then removing (e.g., laser ablating) the material from desired regions of the medical balloon to provide coated regions (e.g., regions with the material thereon) and uncoated regions (e.g., regions with substantially none of the material thereon) about the medical balloon. The coated and uncoated regions can be arranged such that when the medical balloon is folded (e.g., deflated and folded) substantially only the coated regions or substantially only the uncoated regions are exposed about the outer surface of the folded medical balloon, and when the medical balloon is inflated both the coated regions and the uncoated regions are exposed about the outer surface of the inflated medical balloon.

Figure 1:
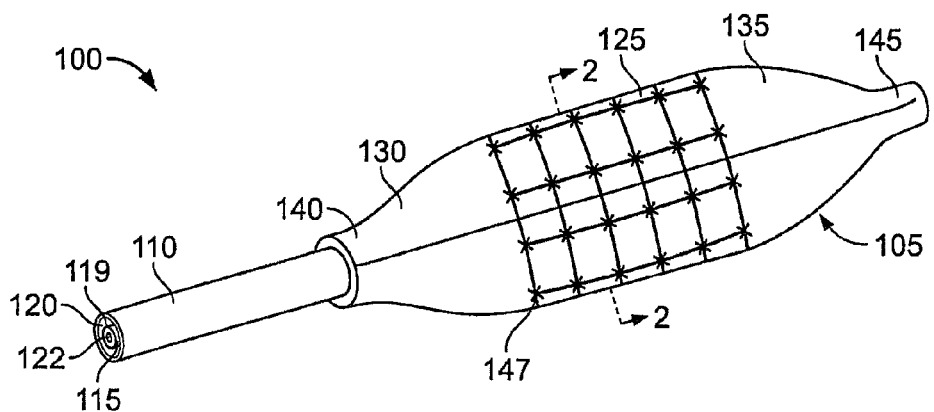
FIG. 1 is a perspective view of an embodiment of a balloon catheter in a deflated state.
Figure 2:
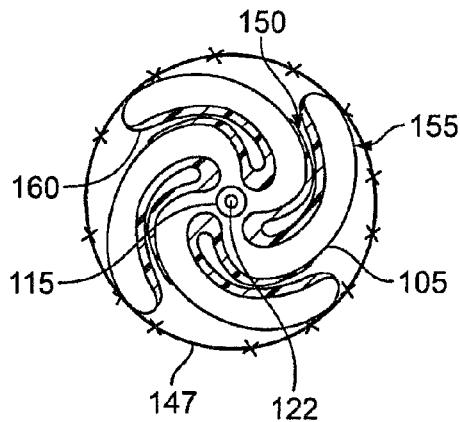
FIG. 2 is a cross-sectional view taken along line 2-2 in FIG. 1.

FIGS. 1 and 2 illustrate a balloon catheter 100 with a balloon 105 in a deflated and folded configuration and a stent 147 disposed about the deflated and folded balloon 105. Referring to FIG. 1, balloon catheter 100 includes an outer tubular member 110 and an inner tubular member 115 extending through a central lumen 119 of outer tubular member 110. An annular inflation lumen 120 is formed between the inner surface of outer tubular member 110 and the outer surface of inner tubular member 115. A guide wire lumen 122 extends axially through inner tubular member 115. A distal portion of inner tubular member 115 extends beyond a distal end of outer tubular member 110. Balloon 105 includes a body portion 125, proximal and distal cone portions 130, 135, and proximal and distal waist portions 140, 145. Proximal waist portion 140 is secured to a distal end region of outer tubular member 110, and distal waist portion 145 is secured to a distal end region of inner tubular member 115. Stent 147 is disposed about body portion 125 of balloon 105.

Balloon 105, as shown in FIG. 2, is folded about inner tubular member 115 and includes inner fold regions (e.g., regions of the balloon that are not exposed about the outer surface of the balloon when the balloon is folded) 150 and outer fold regions (e.g., regions of the balloon that are exposed about the outer surface of the balloon when the balloon is folded) 155. Inner fold regions 150 are coated with a lubricant 160, and outer fold regions 155 are substantially uncoated. For example, about 40 percent or less (e.g., about 30 percent or less, about 20 percent or less, about ten percent or less, about five percent or less) of the surface area of outer fold regions 155 can be coated with lubricant 160. Substantially only the uncoated, outer fold regions 155 of balloon 105 are exposed about the outer surface of the folded balloon 105. Thus, stent 147 is in contact with substantially only the uncoated, outer fold regions 155 of balloon 105, which can help to secure stent 147 to balloon 105.

Figure 3:
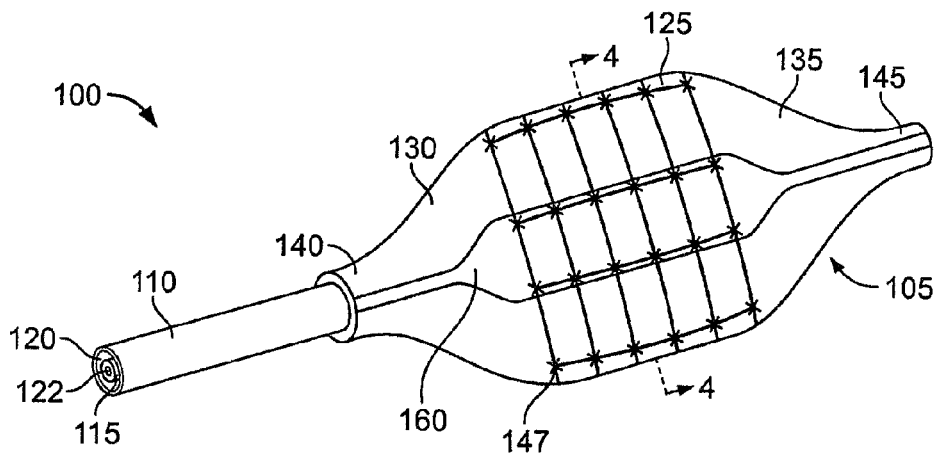
FIG. 3 is a perspective view of an embodiment of a balloon catheter in an inflated state.
Figure 4:
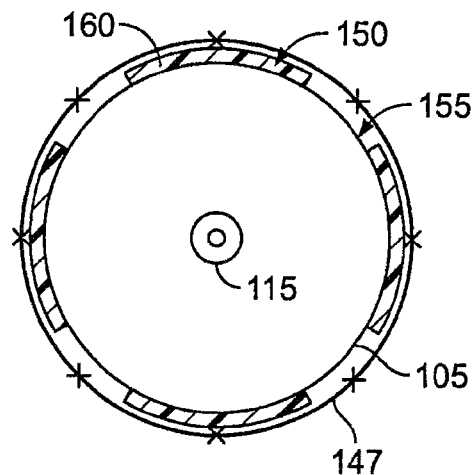
FIG. 4 is a cross-sectional view taken along line 4-4 in FIG. 3.

Referring to FIGS. 3 and 4, when balloon 105 is inflated, both inner fold regions 150 and outer fold regions 155 become exposed along the outer surface of the inflated balloon 105. Consequently, the outer surface of inflated balloon 105 includes regions with lubricant 160 thereon and regions substantially without lubricant 160 thereon, and thus the overall coefficient of friction of the exposed outer surface of the inflated balloon is decreased relative to the exposed outer surface of balloon 105 in the folded configuration. The reduced overall coefficient of friction of the exposed outer surface of balloon 105 can help to decrease the amount of friction encountered by balloon 105 as balloon 105 is withdrawn from stent 147 and from a body vessel (e.g., a blood vessel) during use, as discussed below.

Balloon 105 can include (e.g., can be formed of) one or more biocompatible materials suitable for use in a medical device. In some embodiments, balloon 105 includes one or more thermoplastics. Examples of thermoplastics include polyolefins, polyamides (e.g., nylon 12, nylon 11, nylon 6/12, nylon 6, nylon 66), polyesters, polyethers, polyurethanes, polyureas, polyvinyls, polyacrylics, fluoropolymers, copolymers and/or block copolymers thereof (e.g., block copolymers of polyether and polyamide), and mixtures thereof. Balloon 105 can alternatively or additionally be formed of one or more thermosets. Examples of thermosets include elastomers (e.g., EPDM, epichlorohydrin, nitrile butadiene elastomers, silicones), epoxies, isocyanates, polycaprolactone, poly(dimethylsiloxane) containing polyurethanes and ureas, and polysiloxanes.

Lubricant 160 can have a coefficient of friction that is less than a coefficient of friction of the balloon material(s) in the region of balloon 105 from which lubricant 160 was removed. Lubricant 160 can include one or more biocompatible materials. In certain embodiments, lubricant 160 includes one or more hydrophilic materials and/or one or more hydrophobic materials (e.g., one or more silicones). Other types of lubricants, such as Bioslide® coating produced by SciMed, can alternatively or additionally be used.

Figure 5A:
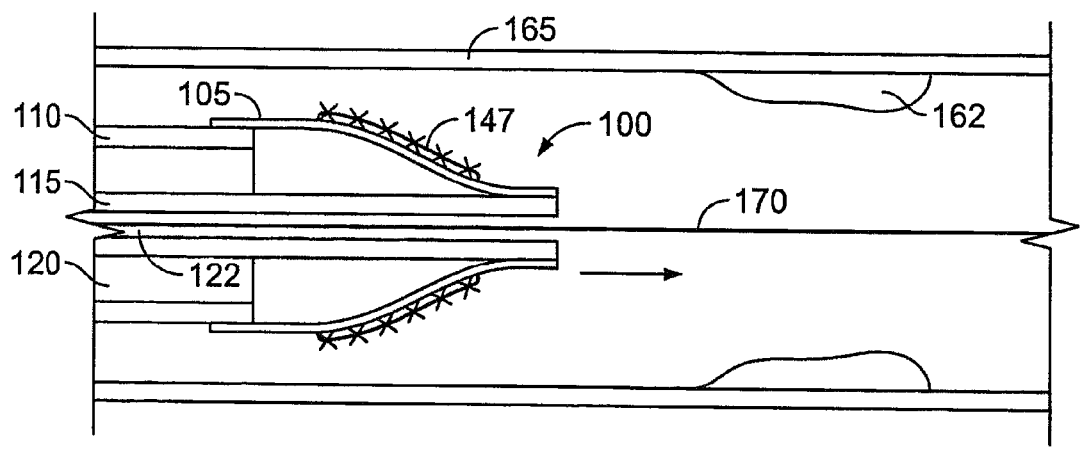
FIGS. 5A-5E illustrate an embodiment of a method of using a balloon catheter.
Figure 5B:
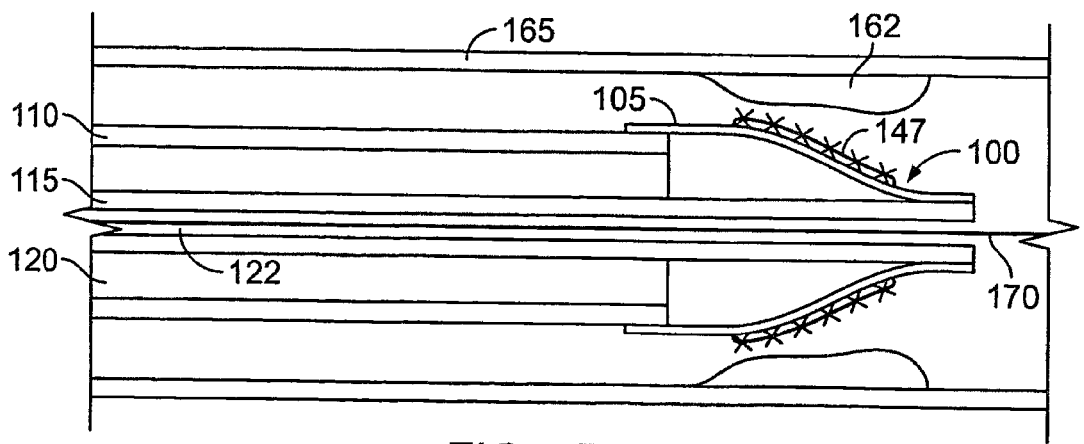
Figure 5C:
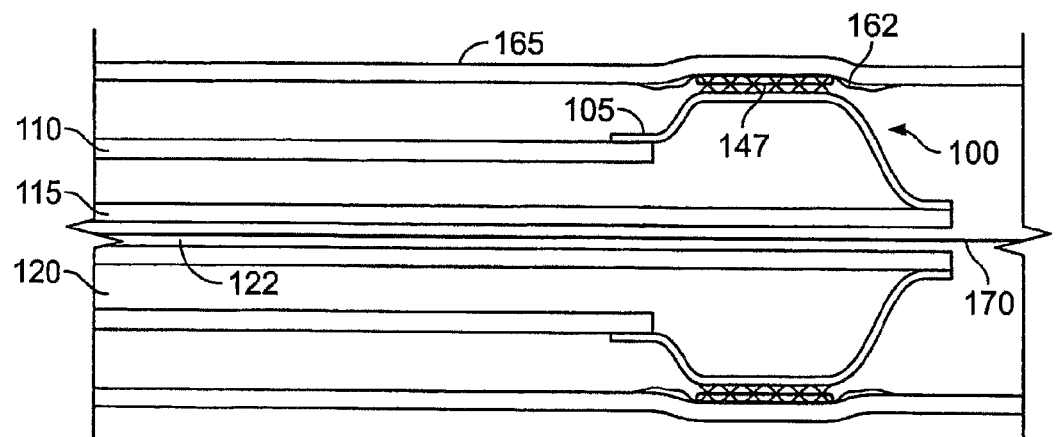

FIGS. 5A-5E illustrate an embodiment of a method of using balloon catheter 100 to deploy stent 147 within an occluded region 162 of a blood vessel 165 of a subject. Referring to FIG. 5A, a guide wire 170 is inserted into blood vessel 165, and then a distal portion of balloon catheter 100 is threaded over guide wire 170. As the distal portion of balloon catheter 100 is threaded over guide wire 170, guide wire 170 becomes disposed within guide wire lumen 122 of inner tubular member 115. Balloon catheter 100, as shown in FIG. 5B, is navigated through blood vessel 165 until balloon 100, about which stent 147 is disposed, is positioned within occluded region 162 of blood vessel 165. Substantially only the uncoated, outer fold regions 155 (FIG. 2) of balloon 105 are exposed about the outer surface of balloon 105 when balloon 105 is folded. Thus, stent 147 is carried by the uncoated, outer fold regions 155 of the folded balloon. Due to frictional resistance between stent 147 and outer fold regions 155 of the folded balloon 105, stent 147 can be restrained (e.g., axially and/or circumferentially restrained) on balloon 105 while balloon 105 and stent 147 are navigated through blood vessel 165. Referring to FIG. 5C, after positioning balloon 105 and stent 147 as desired within blood vessel 165, balloon 105 is inflated to deploy stent 147. Balloon 105 can be inflated by passing an inflation fluid through inflation lumen 120 to balloon 105. Upon inflating balloon 105, both the coated, inner fold regions 150 and the uncoated, outer fold regions 155 are exposed about the outer surface of the inflated balloon 105. Thus, the overall coefficient of friction of the balloon 105 in the inflated configuration is reduced relative to the coefficient of friction of balloon 105 in the folded configuration. The deployed stent can dilate occluded region 162 and thus enable increased blood flow through vessel 165.

Figure 5D:
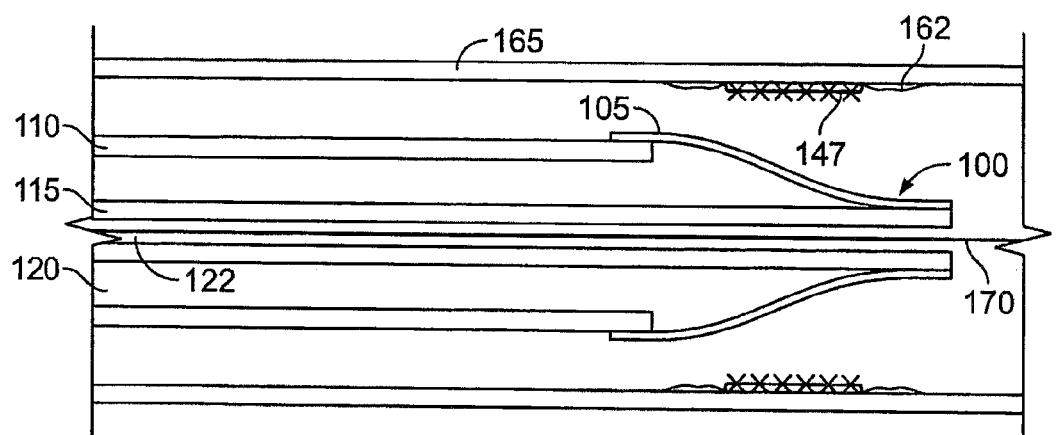
Figure 5E:
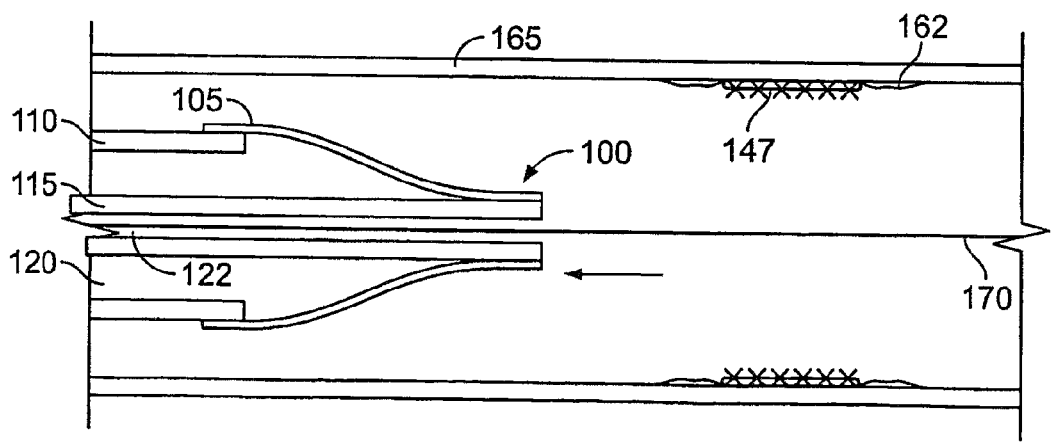

After deploying stent 147, balloon 105 is deflated, as shown in FIG. 5D, so that balloon catheter 100 can be removed from blood vessel 165. Balloon 105 can, for example, be deflated by withdrawing the inflation fluid from balloon 105 via inflation lumen 120. Referring to FIG. 5E, after deflating balloon, balloon catheter 100 and guide wire 170 are removed from blood vessel 165. The presence of lubricant 160 on the surface of inflated balloon 105 can reduce the likelihood of balloon 105 sticking to stent 147. Consequently, balloon 105, after being deflated, can be more easily moved axially relative to stent 147 and the blood vessel wall as balloon catheter 100 is removed from blood vessel 165.

FIGS. 6A-6D illustrate an embodiment of a method of arranging lubricant 160 in a desired configuration about balloon 105. Referring to FIG. 6A, balloon 105 is held in an inflated state and a lubricant applicator 175 is activated to apply lubricant 160 to the outer surface of balloon 105. As shown, in this embodiment, lubricant applicator 175 is a spray gun adapted to spray lubricant 160 onto balloon 105. While only one lubricant applicator is illustrated, multiple applicators can be used. Multiple applicators can, for example, be arranged about the length and/or about the circumference of balloon 105. In some embodiments, lubricant 160 is applied to substantially the entire outer circumference of balloon 105, as shown in FIG. 6B. Lubricant can also be applied along substantially the entire length of balloon 105 (e.g., along body portion 125, cone portions 130, 135, and waist portions 140, 145 of balloon 105). Lubricant 160 can be applied such that the thickness of lubricant 160 is substantially uniform about the circumference and length of balloon 105. The layer of lubricant 160 on balloon 105 can, for example, have a thickness of at least about one micrometer and/or at most about five micrometers (e.g., about one micrometer to about five micrometers). Lubricant applicator 175 can be rotated about balloon 105, as indicated by arrow A in FIG. 6A, to help ensure that substantially the entire outer circumference of balloon 105 is coated with lubricant 160. Lubricant applicator 175 can similarly be moved axially along balloon 105 to help ensure that substantially the entire length of balloon 105 is coated with lubricant 160. Alternatively or additionally, balloon 105 can be rotated and/or moved axially while applicator 175 sprays lubricant 160 onto the outer surface of balloon 105.

As an alternative to or in addition to applying lubricant 160 to balloon 105 by spraying the lubricant onto balloon 105, other techniques can be used to apply lubricant 160 to balloon 105. Examples of such techniques include painting, dip coating, and pad printing.

In some embodiments, after applying lubricant 160 to balloon 105, the lubricant is cured. Lubricant 160 can, for example, be cured by applying UV light to the lubricant. Curing lubricant 160 can help to ensure that lubricant 160 remains secured to the outer surface of balloon 105 and intact throughout the manufacturing and delivery processes described herein.

Referring to FIG. 6C, after applying lubricant 160 to the outer surface of balloon 105, balloon 105 is deflated. Upon being deflated, balloon 105 forms multiple (e.g., four) circumferentially spaced wings 190 that form peaks 180 and valleys 185 about the circumference of balloon 105. Various techniques can be used to help ensure that balloon 105 forms wings 190 as it is deflated. For example, circumferentially spaced regions of the balloon surface can be heat-treated to help form wings 190. In some embodiments, the heat-treated regions of the balloon surface correspond to valleys 185 of the deflated balloon. The balloon material in the heat-treated regions can, for example, be modified so that the heat-treated regions of the balloon surface collapse inwardly to form valleys 185 when balloon 105 is deflated. Alternatively, the material of balloon 105 in the heat-treated regions can be modified to resist collapse, causing the unmodified region to collapse inward first, forming valleys 185. Examples of heat-treatment techniques are described in U.S. application Ser. No. 11/599,049 [Publication no. 2008/0114294], entitled "Medical Balloon Deflation," and filed concurrently herewith, which is incorporated by reference herein.

As an alternative to or in addition to the heat-treatments described above, circumferentially spaced channels or depressions can be formed in the balloon wall to facilitate the formation of wings 190. The depressions or channels can, for example, serve as preferential folding portions, which can help to form wings 190 upon deflation of balloon 105. For example, the depressions or channels can collapse inwardly to form valleys 185 when balloon 105 is deflated. In certain embodiments, the depressions or channels can be formed using laser ablation techniques. Examples of balloons including channels for preferential folding are described in Ser. No. 11/060,151, entitled "Medical Devices," filed Feb. 17, 2005 and published as US 2006/0182873, which is incorporated by reference herein.

As shown in FIG. 6D, after deflating the lubricated balloon 105, the lubricated balloon 105 is folded into a preset, compact configuration. Balloon 105 can, for example, be folded into this configuration by engaging (e.g., grasping) wings 190 with a chuck, and rotating the chuck. In certain embodiments, balloon 105 is folded while being heat-treated, as described in U.S. Pat. No. 5,209,799, which is incorporated by reference herein. Balloon 105 can alternatively or additionally be folded using one or more other known techniques. In the folded configuration, as discussed above, balloon 105 includes inner fold regions 150 and outer fold regions 155. Outer fold regions 155 are exposed about the outer surface of the folded balloon 105, while inner fold regions 150 are at least partially covered by outer fold regions 155, and thus are not exposed about the outer surface of the folded balloon 105.

Figure 6F:
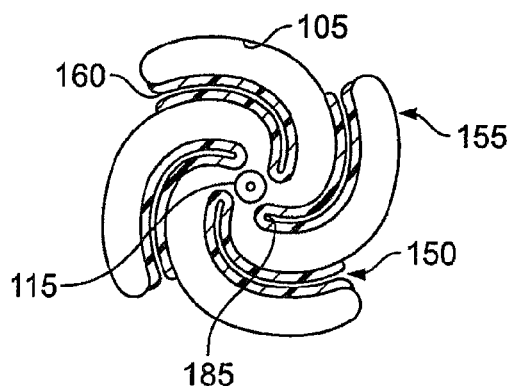

Referring to FIG. 6E, after folding the lubricated balloon 105, a laser device (e.g., a UV light laser) 195 is activated to apply laser energy (e.g., UV light) to the exposed lubricant 160 on outer fold regions 155 of balloon 105. As a result, lubricant 160 is removed (e.g., ablated) from outer fold regions 155. In some embodiments, as shown in FIG. 6F, lubricant 160 is removed from substantially the entire outer circumference of folded balloon 105. Laser device 195 can, for example, be moved about the circumference of the folded balloon 105, as indicated by arrow B in FIG. 6E, to help ensure that substantially all of the exposed lubricant 160 about the outer circumference of the folded balloon 105 (e.g., substantially all of the lubricant 160 overlying outer fold regions 155) is removed from balloon 105. The laser energy can alternatively be applied in a manner to remove only portions of lubricant 160 from the outer circumference of the folded balloon 105. In some embodiments, for example, the laser energy is applied to circumferentially space regions of the outer surface of the folded balloon 105 such that substantially only the lubricant 160 in those circumferentially spaced regions is removed from balloon 105. Alternatively or additionally, lubricant 160 can be removed from substantially only a desired region (e.g., substantially only the right-hemisphere, substantially only the left hemisphere, etc.) of the folded balloon 105.

In certain embodiments, lubricant 160 is removed from substantially the entire length of balloon 105 (e.g., from body portion 125, cone portions 130, 135, and waist portions 140, 145). Laser device 195 can, for example, be moved axially along balloon 105 to help ensure that the exposed lubricant 160 is removed from substantially the entire length of balloon 105. The laser energy can alternatively be applied in a manner to remove lubricant 160 from only certain regions along the length of balloon 105. In some embodiments, for example, laser energy is applied substantially only to body portion 125 of balloon 105 such that substantially only lubricant 160 overlying body portion 125 is removed from balloon 105. By removing lubricant 160 from body portion 125, the coefficient of friction of the exposed surfaces of body portion 125 is increased, and thus the ability of body portion 125 to carry stent 147 thereon can be improved. This can, for example, reduce the likelihood of stent 147 slipping on the surface of balloon 105 (e.g., slipping off the balloon entirely). Additionally, by leaving lubricant on the exposed surfaces of those regions of balloon 105 that do not contact stent 147 (e.g. cone portions 130, 135 and waist portions 140, 145), the coefficient of friction of those regions of balloon 115 can be maintained at a relatively high value (e.g., at the value of the coefficient of friction of the lubricant), and thus the frictional resistance experienced by those regions of balloon 105 as balloon 105 is navigated through blood vessel 165 can be reduced.

While laser device 195 has been described as being rotatable and axially moveable relative to balloon 105, the folded balloon 105 can alternatively or additionally be rotatable and/or axially moveable relative to laser device 195 to help ensure the exposed lubricant 160 is removed from all desired regions of balloon 105.

The depth of ablation caused by the laser energy emitted from laser device 195 can be controlled by adjusting certain parameters of the laser energy, such as the wavelength of the incident light and/or the energy fluence ($J/cm^2$). In some embodiments, UV light having a wavelength of about 157 nm to about 450 nm (e.g., about 157 nm to about 350 nm, about 157 nm, about 193 nm, about 248 nm, about 308 nm, about 351 nm, about 355 nm, about 450 nm) is used. The wavelength of the laser can be selected such that the laser energy removes the lubricant without substantially affecting the balloon material. In certain embodiments, the UV light is applied in pulses to help control the depth to which the laser energy penetrates lubricant 160 and balloon 105. Laser device 195 can, for example, be pulsed in a manner that allows substantially all of the lubricant 160 overlying a targeted region of balloon 105 to be removed without substantially affecting the balloon material in the targeted region.

Figure 6G:
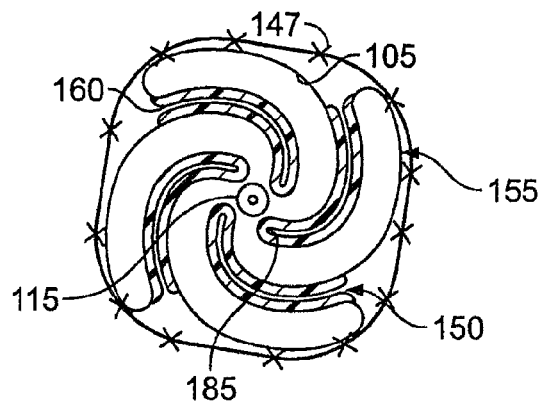

As shown in FIG. 6G, after removing lubricant 190 from outer fold regions 155 of balloon 105, stent 147 is disposed about body portion 125 of balloon 105. Because lubricant 160 was removed from outer fold regions 155 of balloon 105, stent 147 rests on the exposed balloon material in outer fold regions 155. Because the exposed balloon material has a higher coefficient of friction than lubricant 160, this arrangement can help to retain stent 147 in a desired position about balloon 105 (e.g., about body portion 125 of balloon 105) during use.

While embodiments above include applying laser energy to regions of lubricant 160 exposed about the outer surface of balloon 105 after balloon 105 has been folded, laser energy can alternatively or additionally be applied to regions of lubricant 160 on the outer surface of balloon 105 prior to folding balloon 105 in order to remove those regions of lubricant 160. For example, after coating the inflated balloon 105 with lubricant 160, regions of lubricant 160 overlying regions of the inflated balloon 105 that correspond to outer fold regions 155 of balloon 105 in the deflated and folded configuration (e.g., the regions of balloon 105 that will be exposed about the outer surface of balloon 105 when balloon 105 is deflated and folded) are laser ablated to remove those regions of lubricant 160 from the inflated balloon 105. In certain embodiments, the regions of the inflated balloon 105 that correspond to outer fold regions 155 of the folded balloon 105 are visible on the outer surface of the inflated balloon 105. The laser energy can be focused on those visible regions to remove lubricant 160 overlying those visible regions. The application of the laser energy can, for example, be controlled by a motion control system within the laser processing machine, the laser can be applied substantially only to those visible regions. As a result of removing lubricant 160 from those regions of the inflated balloon 105 that correspond to outer fold regions 155 of balloon 105 in the folded configuration, substantially only the uncoated, outer fold regions 155 are exposed about the outer surface of the folded balloon 105 after deflating and folding the partially coated balloon 105.

In some embodiments, a masking device is used to help focus the laser energy onto those regions in which it is desired to remove the lubricant. The masking device can, for example, be temporarily disposed about the balloon during the laser treatment process. In certain embodiments, the masking device is adhesively fixed to the outer surface of balloon 105 during the laser treatment process. Other techniques can alternatively or additionally be used to hold the masking device in a substantially fixed position relative to balloon 105. In some embodiments, the masking device is a tubular member. The masking device can be arranged about balloon 105 such that regions of the masking device that are permeable to laser energy (e.g., permeable to UV laser light) overlie the regions of lubricant 160 to be ablated, and regions of the masking device that are impermeable to laser energy overlie the remaining regions of lubricant 160. In certain embodiments, the laser impermeable regions of the masking device are formed of one or more laser impermeable materials, such as one or more metals. In certain embodiments, the masking device can include one or more apertures in those regions where laser permeability is desired. In some embodiments, for example, the masking device is a solid tube forming multiple slots that extend therethrough. After fixing the masking device about balloon 105 as desired, the laser energy is applied to those regions of lubricant 160 underlying the laser permeable regions of the masking device. By using the masking device, broader and/or less precise lasers can be used to ablate the desired regions of lubricant 160 without substantially ablating other regions of lubricant 160.

In certain embodiments, laser energy is applied to regions of lubricant 160 in a predetermined pattern. The laser energy can, for example, be applied to circumferentially spaced regions of lubricant 160 on the inflated balloon 105. Subsequently, balloon 105 can be deflated and folded. A balloon form and folder can, for example, be used to fold balloon 105. Blades of the balloon form and folder can be manually aligned with those regions from which lubricant 106 was removed, which are visible. This can help to ensure that those regions from which lubricant 106 was removed fall within desired fold regions of balloon 105.

Figure 7:
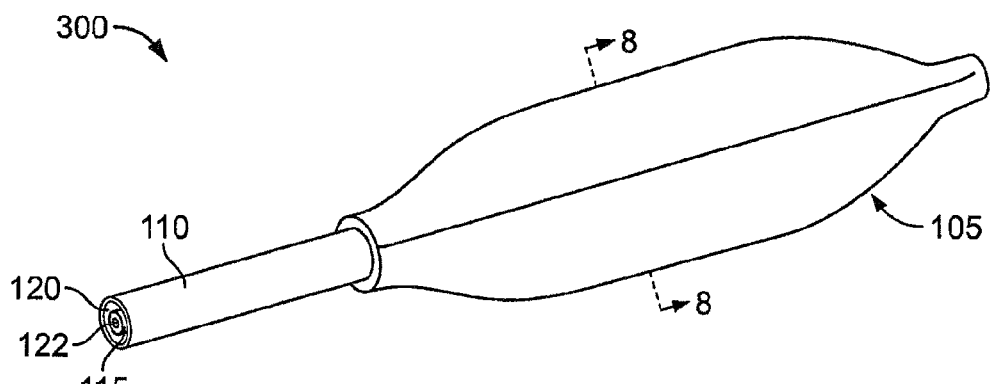
FIG. 7 is a perspective view of an embodiment of a balloon catheter in an uninflated state.
Figure 8:
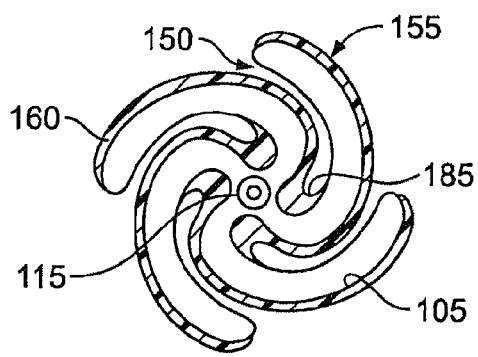
FIG. 8 is a cross-sectional view taken along line 8-8 in FIG. 7.

While balloon 105 has been described as having lubricated surface regions (e.g., inner fold regions 150) that remain substantially unexposed (e.g., covered) until balloon 105 is inflated, other arrangements are possible. FIGS. 7 and 8, for example, illustrate a balloon catheter 300 in a deflated and folded configuration. Balloon catheter 300 is similar to balloon catheter 100 of FIGS. 1-4. As shown in FIG. 8, however, outer fold regions 155 of balloon 105 are coated with lubricant 160, and inner fold regions 150 of balloon 105 are substantially uncoated. For example, about 40 percent or less (e.g., about 30 percent or less, about 20 percent or less, about ten percent or less, about five percent or less) of the surface area of inner fold regions 150 can be coated with lubricant 160. Thus, substantially only the lubricated regions of balloon 105 are exposed about the outer surface of balloon 105 in the folded configuration. This arrangement can help to reduce the amount of friction experienced by balloon 105 during use (e.g., while navigating balloon 105 in the folded state through a blood vessel).

Figure 9:
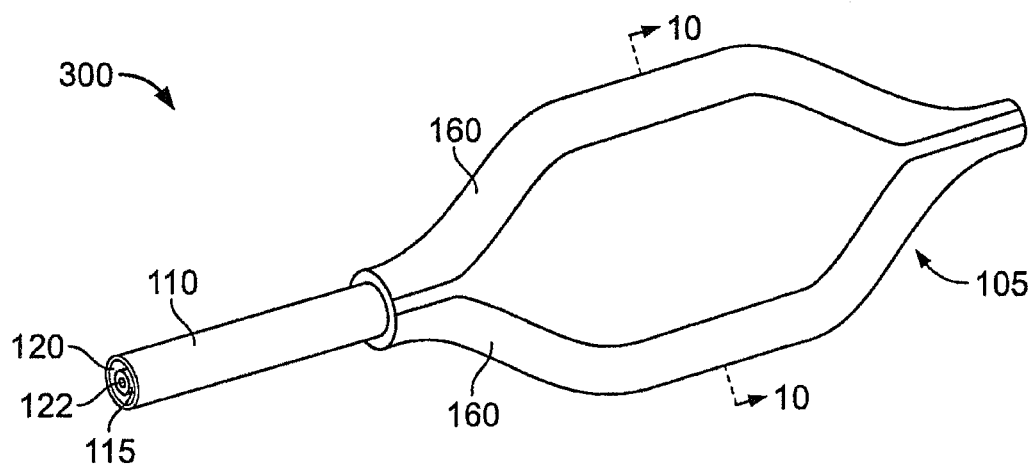
FIG. 9 is a perspective view of an embodiment of a balloon catheter in an inflated state.
Figure 10:
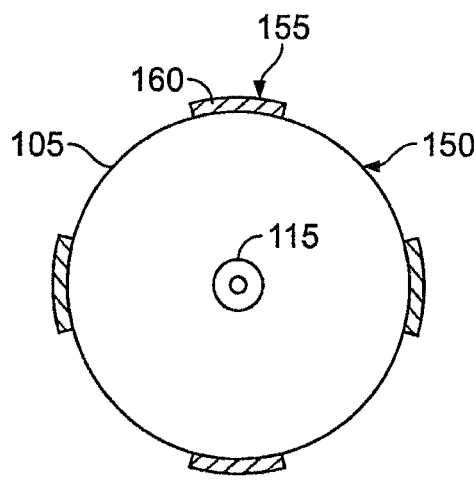
FIG. 10 is a cross-sectional view taken along line 10-10 in FIG. 9.

Referring to FIGS. 9 and 10, when balloon 105 is inflated, both inner fold regions 150 and outer fold regions 155 are exposed about the outer surface of the inflated balloon 105. Consequently, the outer surface of the inflated balloon 105 includes regions with lubricant 160 thereon and regions with substantially no lubricant thereon. Exposing the uncoated regions of the inflated balloon 105 can, for example, help to increase the friction between the inflated balloon 105 and the blood vessel wall during use. As a result, the stability of the inflated balloon 105 within the blood vessel can be increased as compared to a fully coated balloon.

Figure 11A:
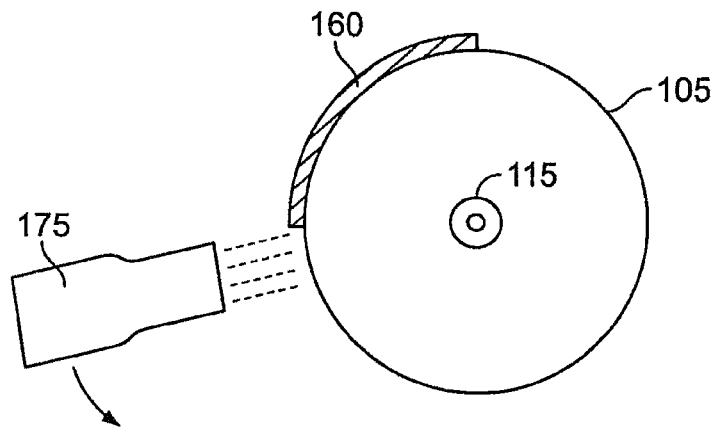
FIGS. 11A-11F illustrate a method of manufacturing a balloon catheter.
Figure 11B:
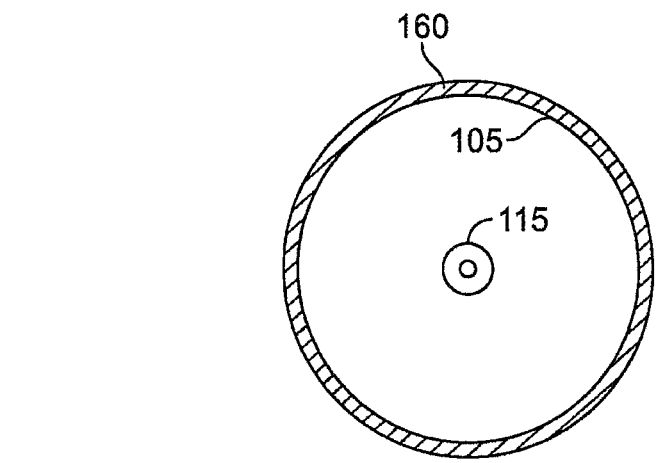
Figure 11C:
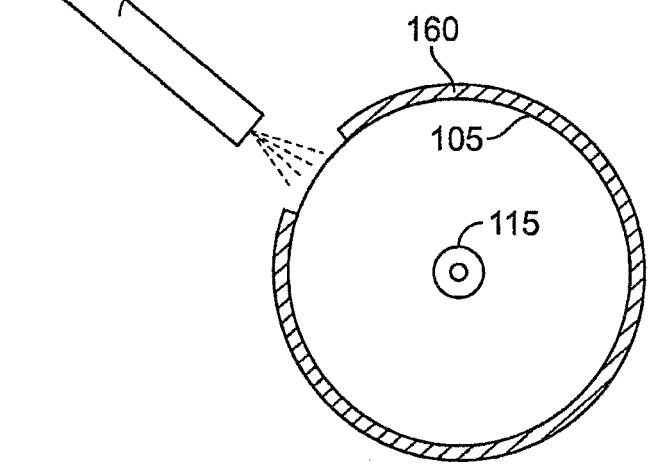

FIGS. 11A-11D illustrate an embodiment of a method of manufacturing balloon catheter 300. Referring to FIG. 11A, balloon 105 of balloon catheter 300 is held in an inflated configuration and lubricant 160 is applied to the outer surface of balloon 105. Lubricant 160 is applied to substantially the entire circumference of balloon 105, as shown in FIG. 11B. Referring to FIG. 11C, after applying lubricant 160 to balloon 105, laser energy is applied to desired regions of lubricant 160 to remove the desired regions of lubricant 160 from balloon 105. The laser energy can, for example, be applied to regions of lubricant 160 overlying regions of the inflated balloon that correspond to one or more of inner fold regions 150 of balloon 105 in the folded configuration. In certain embodiments, a masking device is used to focus the laser energy on substantially only those regions of the balloon 105 from which it is desired to remove lubricant 160. Any of the masking devices described above can be used. Other devices and/or techniques can alternatively or additionally be used.

Figure 11D:
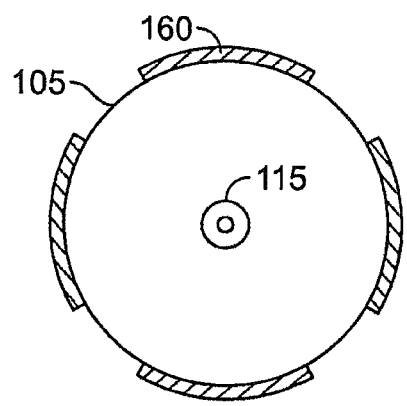
Figure 11E:
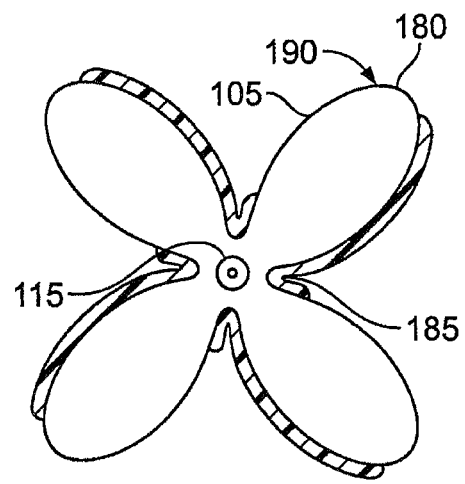
Figure 11F:
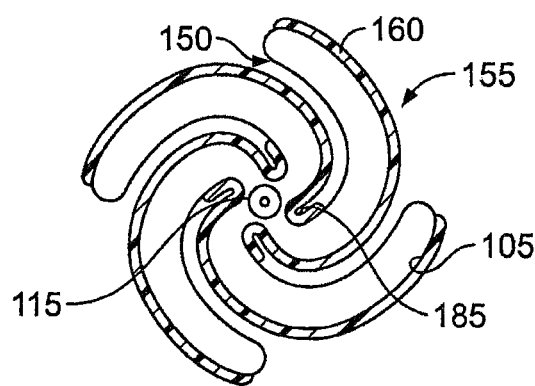

After laser ablating the desired regions of lubricant 160, the outer surface of the inflated balloon 105 includes lubricant coated regions and substantially uncoated regions, as shown in FIG. 11D. In some embodiments, lubricant covers about 50 percent or more (e.g., about 60 percent or more, about 70 percent or more, about 80 percent or more, about 90 percent or more) and/or about 90 percent or less (e.g., about 80 percent or less, about 70 percent or less, about 60 percent or less, about 50 percent or less) of the outer surface of the inflated balloon 105. Referring to FIG. 11E, balloon 105 is then deflated to form wings 190. After deflating balloon 105, balloon 105 is folded into a compact configuration, as shown in FIG. 11F, such that the lubricated regions (e.g., substantially only the lubricated regions) of balloon 105 are exposed about the outer surface of the folded balloon 105. Any of the folding techniques described above can be used to fold balloon 105 into this configuration. A balloon form and folder can, for example, be used to fold balloon 105. Blades of the balloon form and folder can be manually aligned with those regions from which lubricant 106 was removed, which are visible. This can help to ensure that those regions from which lubricant 106 was removed fall within desired fold regions of balloon 105.

Balloon catheter 300 can be used to perform various medical treatments, such as angioplasty procedures. To perform an angioplasty procedure, balloon catheter 300 can be navigated through a blood vessel until balloon 105 is positioned within an occluded region of the blood vessel. Due to the lubricated outer surface (e.g., the lubricated outer fold regions 155) of balloon 105, balloon catheter 300 can be navigated through blood vessel 165 with reduced friction as compared to a balloon catheter with an uncoated balloon. Balloon 105, after being positioned in the occluded region, can be inflated, dilating the occluded region. When balloon 105 is inflated, both coated and uncoated surface regions of balloon 105 are exposed about the outer surface of the inflated balloon 105. Due to the relatively high coefficient of friction of the uncoated regions (e.g., the inner fold regions 150) as compared to the coated regions (e.g., the outer fold regions 155), the exposure of the uncoated regions about the outer surface of the inflated balloon 105 can help to stabilize (e.g., axially and/or circumferentially stabilize) balloon 105 against the occluded region of the vessel and/or the vessel wall as the occluded region is dilated. This can help balloon 105 to maintain a desired axial and/or circumferential position while inflated. After dilating the occluded region, balloon 105 can be deflated and balloon catheter 300 can be removed from the blood vessel 165.

While certain embodiments have been described, other embodiments are possible.

As an example, while methods above describe lubricant 160 as being applied to substantially the entire surface of balloon 105, lubricant 160 can alternatively be applied to only certain regions of balloon 105. In certain embodiments, for example, lubricant is applied to only body portion 125 of balloon 105. Lubricant can alternatively or additionally be applied to one or more other regions of balloon 105. In some embodiments, lubricant 160 is applied to circumferentially spaced regions of balloon 105. In certain embodiments, for example, applying lubricant to circumferentially spaced regions of balloon 105 can help to reduce the amount laser ablation used in later stages of the manufacturing process.

As another example, while balloon 105 has been described as being deflated into a configuration including four wings 190 extending radially outward, any of various other deflation configurations that allow balloon 105 to be folded in a manner such that the outer surface of the folded balloon includes exposed regions (e.g., outer fold regions 155) and covered regions (e.g., inner fold regions 150) can be used. In certain embodiments, for example, balloon 105 is configured to be deflated into fewer than four wings (e.g., three wings, two wings, one wing). In some embodiments, balloon 105 is configured to be deflated into more than four wings (e.g., five wings, six wings, seven wings, eight wings). The number of wings can, for example, depend on the size of the balloon. In certain embodiments, balloon 105 is configured to fold in a helical configuration. In such embodiments, a helical fold region can be imparted along the outer surface of balloon 105 by, for example, heat-treating and/or laser-treating the surface of balloon 105 along the desired helical folding path.

As a further example, while lubricant 160 has been described as being applied in a manner to have a substantially uniform thickness about the circumference and length of balloon 105, lubricant 160 can alternatively vary in thickness about the circumference and/or length of balloon 105. In certain embodiments, for example, lubricant 160 is applied such that the thickness of lubricant 160 is greater at the distal end regions (e.g., at distal cone portion 135 and distal waist portion 145) than at the proximal end regions (e.g., at proximal cone portion 130 and proximal waist portion 140) of balloon 105. This arrangement can help to ensure that the distal end regions of balloon 105, which can experience greater amounts of friction during delivery of balloon 105 through a blood vessel, include a sufficient amount of lubricant to reduce friction experienced by the balloon catheter during delivery.

As another example, while methods above describe removing lubricant from the balloon using laser energy, other material removal techniques can be used.

As an additional example, while the methods described above include applying lubricant 160 to balloon 105, one or more other material types can alternatively or additionally be applied to balloon 105. In some embodiments, a relatively tacky material is applied to the outer surface of balloon 105. The relatively tacky material can have a coefficient of friction that is greater than the coefficient of friction of the balloon material(s). Examples of tacky materials include certain urethanes (e.g., urethane in a solution). After applying the tacky material to balloon 105, regions of the tacky material overlying inner fold regions 150 of balloon 105 can be removed (e.g., by laser ablation) such that, when balloon 105 is folded, the exposed outer surface of the folded balloon includes the tacky material thereon. The tacky material can thus help to retain stent 147 on balloon 105. Upon inflating balloon 105 to deploy stent 147, those regions of balloon 105 from which the tacky material was removed will become exposed about the outer surface of the inflated balloon, and will thus reduce the overall coefficient of friction of the outer surface of the inflated balloon. As a result, the balloon can be removed from stent 147 and the vessel within which stent 147 is deployed with reduced resistance as compared to a balloon having a surface completely covered by the tacky material.

The tacky material can alternatively or additionally be applied to inner fold regions 150 of balloon 105. Applying the tacky material to inner fold regions 150 can help to secure (e.g., axially and/or circumferentially secure) balloon 105 when balloon 105 is inflated within the blood vessel.

Other materials can alternatively or additionally be applied to balloon 105. For example, drug-eluting coatings can be applied to the balloon. In some embodiments, the drug-eluting coating is configured in an arrangement similar to the lubricant in FIGS. 1-4 such that the drug-eluting coating is not exposed about the outer surface of the balloon when the balloon is folded and the coating is exposed about the outer surface of the balloon when the balloon is inflated. In such embodiments, the drug can be eluted from the coating upon inflating the balloon. The drug-eluting coating can, for example, be biodegradable such that upon exposing the coating to blood when the balloon is inflated within a blood vessel, the coating degrades and releases the drug. Other examples of materials that can be applied to the balloon include sacrides, genes, RNA, DNA, etc.

As a further example, while above-described methods of using balloon catheters 100, 300 include inflating balloon 105 within occluded region 162 of blood vessel 165, balloon 105 can alternatively or additionally be inflated within other regions of blood vessels. In some embodiments, for example, balloon 105 is inflated within a weakened region of a blood vessel to deploy stent 147 therein. In certain embodiments, balloon 105 is inflated within a region of a blood vessel to prevent blood flow or to divert the flow of blood through the vessel.

As another example, while embodiments above describe methods of using balloon catheters within a blood vessel, the balloon catheters can alternatively or additionally be deployed within other types of body vessels.

As an additional example, while embodiments above describe the use of stents, other types of implantable medical endoprostheses, such as grafts, stent-grafts, etc. can be used.

Other embodiments are in the claims.

The invention claimed is:

1. A balloon catheter, comprising:
a balloon folded about a catheter shaft, the folded balloon comprising outer fold regions that are substantially exposed about an outer surface of the folded balloon and inner fold regions that are substantially unexposed about the outer surface of the folded balloon, the inner fold regions being coated with a material and the outer fold regions being coated with some of the material, wherein at most about 40 percent of the outer fold regions are coated with the material.

2. The balloon catheter of claim 1, further comprising a stent disposed about the outer surface of the folded balloon.

3. The balloon catheter of claim 1, the balloon being made of a balloon material with a coefficient of friction, the material coated on the inner fold regions having a coefficient of friction that is different than the coefficient of friction of the balloon material.

4. The balloon catheter of claim 3, wherein the coefficient of friction of the material coated on the inner fold regions being less than the coefficient of friction of the balloon material.

5. The balloon catheter of claim 1, the material being a lubricant.

6. The balloon catheter of claim 1, the material being a drug-eluting coating.

7. The balloon catheter of claim 1, the balloon having a proximal end region and a distal end region, the material having a thickness, the thickness of the material at the distal end region of the balloon being greater than at the proximal end region of the balloon.

8. A balloon catheter comprising:
a balloon having an outer surface and comprising a balloon body portion, a first balloon cone portion, a first balloon waist portion, a second balloon cone portion, and a second balloon waist portion;
the balloon further comprising a layer of material on at least a portion of the balloon outer surface;
the balloon in a folded configuration having a plurality of inner fold regions and a plurality of outer fold regions, the plurality of outer fold regions forming the balloon outer surface in the folded configuration;
wherein the layer of material is at least on the inner fold regions of the balloon body portion and is not on the outer fold regions of the balloon body portion;
wherein the layer of material is further on:
each of the inner fold regions of the first balloon cone portion, the first balloon waist portion, the second balloon cone portion, and the second balloon waist portion; and
each of the outer fold regions of the first balloon cone portion, the first balloon waist portion, the second balloon cone portion, and the second balloon waist portion.

9. The balloon catheter of claim 8, the first balloon cone portion and first balloon waist portion forming a proximal balloon end region, the second balloon cone portion and second balloon waist portion forming a distal balloon end region;
the material having a thickness, the thickness of the material at the distal balloon end region being greater than at the proximal balloon end region.

10. The balloon catheter of claim 9, the material being a lubricant.

11. The balloon catheter of claim 8, wherein when the balloon is in an inflated configuration the plurality of inner fold regions and the plurality of outer fold regions form the outer surface of the balloon.

12. The balloon catheter of claim 8, the balloon being in the folded configuration and further comprising a stent disposed about the balloon.

13. The balloon catheter of claim 8, the material being a drug eluting coating.

14. The balloon catheter of claim 8, wherein the layer of material has a uniform thickness.

\* \* \* \* \*